United States Patent
Aston et al.

(10) Patent No.: US 7,037,262 B2
(45) Date of Patent: May 2, 2006

(54) BODY FLUID COLLECTION AND ANALYSIS

(75) Inventors: Roger Aston, Malvern (GB); Leigh T Canham, Malvern (GB)

(73) Assignee: pSiMedica Limited, Malvern (GB)

( * ) Notice: Subject to any disclaimer, the term of this patent is extended or adjusted under 35 U.S.C. 154(b) by 41 days.

(21) Appl. No.: 10/485,358

(22) PCT Filed: Aug. 14, 2002

(86) PCT No.: PCT/GB02/03731

§ 371 (c)(1),
(2), (4) Date: Jan. 30, 2004

(87) PCT Pub. No.: WO03/015636

PCT Pub. Date: Feb. 27, 2003

(65) Prior Publication Data

US 2004/0193030 A1 Sep. 30, 2004

(30) Foreign Application Priority Data

Aug. 18, 2001 (GB) .............................. 0120202

(51) Int. Cl.
*A61B 5/00* (2006.01)

(52) U.S. Cl. ...................... 600/362; 600/310
(58) Field of Classification Search ................ 600/362, 600/365, 366, 306, 345–347, 310, 309, 316, 600/322
See application file for complete search history.

(56) References Cited

U.S. PATENT DOCUMENTS

| 4,756,314 A |   | 7/1988 | Eckenhoff et al. |
| 5,203,327 A |   | 4/1993 | Schoendorfer et al. |
| 5,433,080 A | * | 7/1995 | Boeckel ........................ 62/3.6 |
| 5,433,214 A | * | 7/1995 | Brehm et al. ................ 600/573 |
| 5,874,047 A | * | 2/1999 | Schoning et al. ......... 422/82.02 |
| 5,980,498 A |   | 11/1999 | Brown et al. |
| 6,042,543 A | * | 3/2000 | Warwick et al. ............. 600/362 |
| 6,130,748 A | * | 10/2000 | Kruger et al. ............... 356/450 |
| 6,277,662 B1 | * | 8/2001 | Nagata .......................... 438/22 |
| 6,322,895 B1 | * | 11/2001 | Canham ..................... 428/450 |
| 6,334,856 B1 | * | 1/2002 | Allen et al. .................. 604/191 |
| 2002/0192680 A1 |   | 12/2002 | Chan et al. |

FOREIGN PATENT DOCUMENTS

| GB | 2 303 847 A | 3/1997 |
| GB | 2 324 866 A | 11/1998 |
| WO | WO 87/00413 | 1/1987 |
| WO | WO 9733147 A2 * | 9/1997 |

OTHER PUBLICATIONS

M. Thust et al, Porous Silicon as a Substrate Material for Potentiometric Biosensors, Meas. Sci. Tehcnol., 1996, vol. 7, pp. 26–29.*

P Hurley et al, Partial Oxidation of Porous Silicon, Semicond. Sci. Technol., 1993, vol. 8, pp. 2168–2175.*

Wei et al, "Desorption–ionization mass spectrometry on porous silicon" Nature, Macmillan Journals LTD., London, GB, vol. 399, May 20, 1999, pp. 243–246.

WPI Abstract No. 1998–254402/23 & JP 10080266 A Mar. 31, 1998.

* cited by examiner

*Primary Examiner*—Max F. Hindenberg
*Assistant Examiner*—Navin Natnithithadha
(74) *Attorney, Agent, or Firm*—Nixon & Vanderhye P.C.

(57) ABSTRACT

The invention relates to attachable body fluid collection devices, each comprising at least one storage structure for, when in use, storing a body fluid sample secreted by a body fluid secreting surface. The or at least one of the storage structure comprises silicon. Particular emphasis is placed on sweat patches and techniques for analyzing sweat.

15 Claims, 12 Drawing Sheets

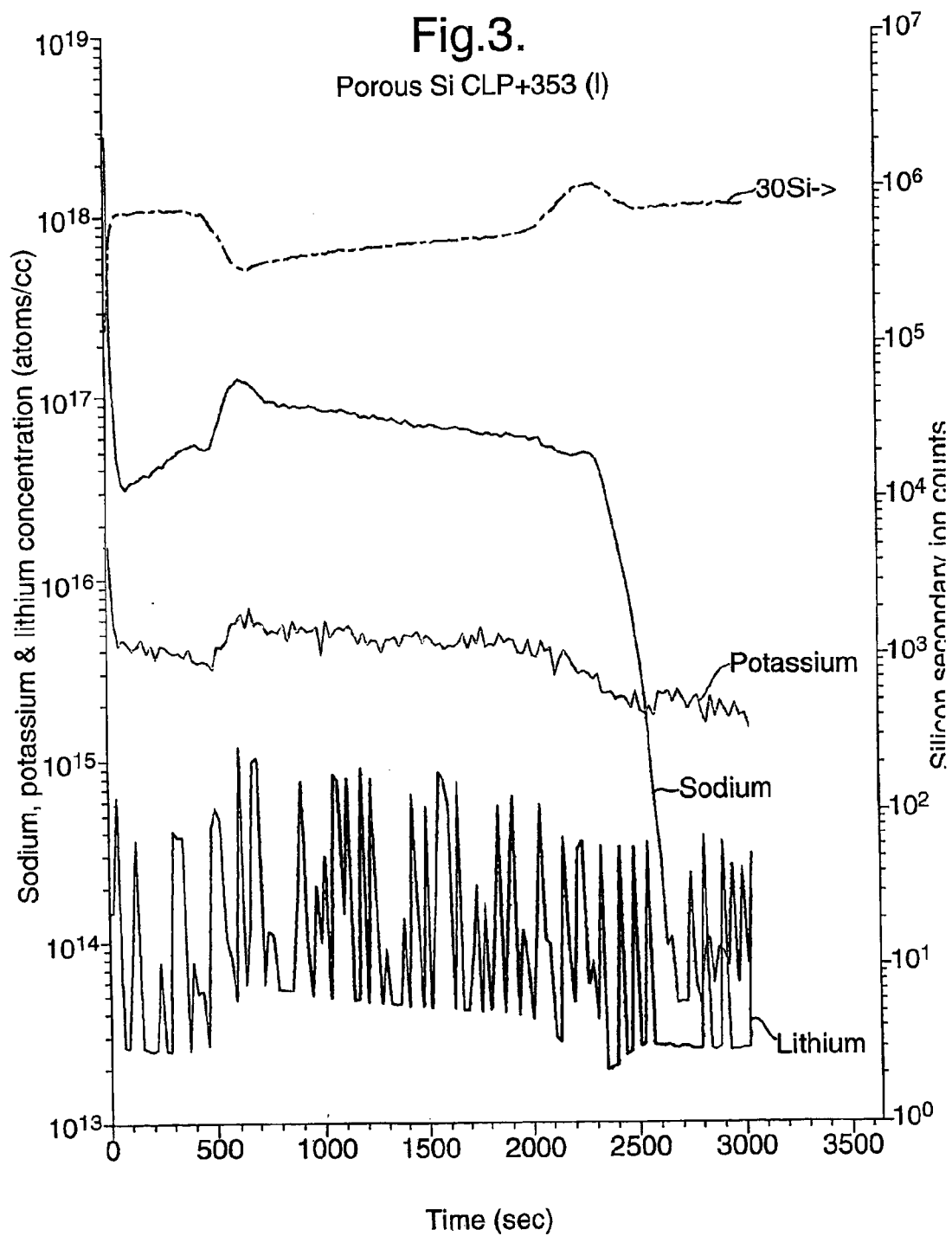

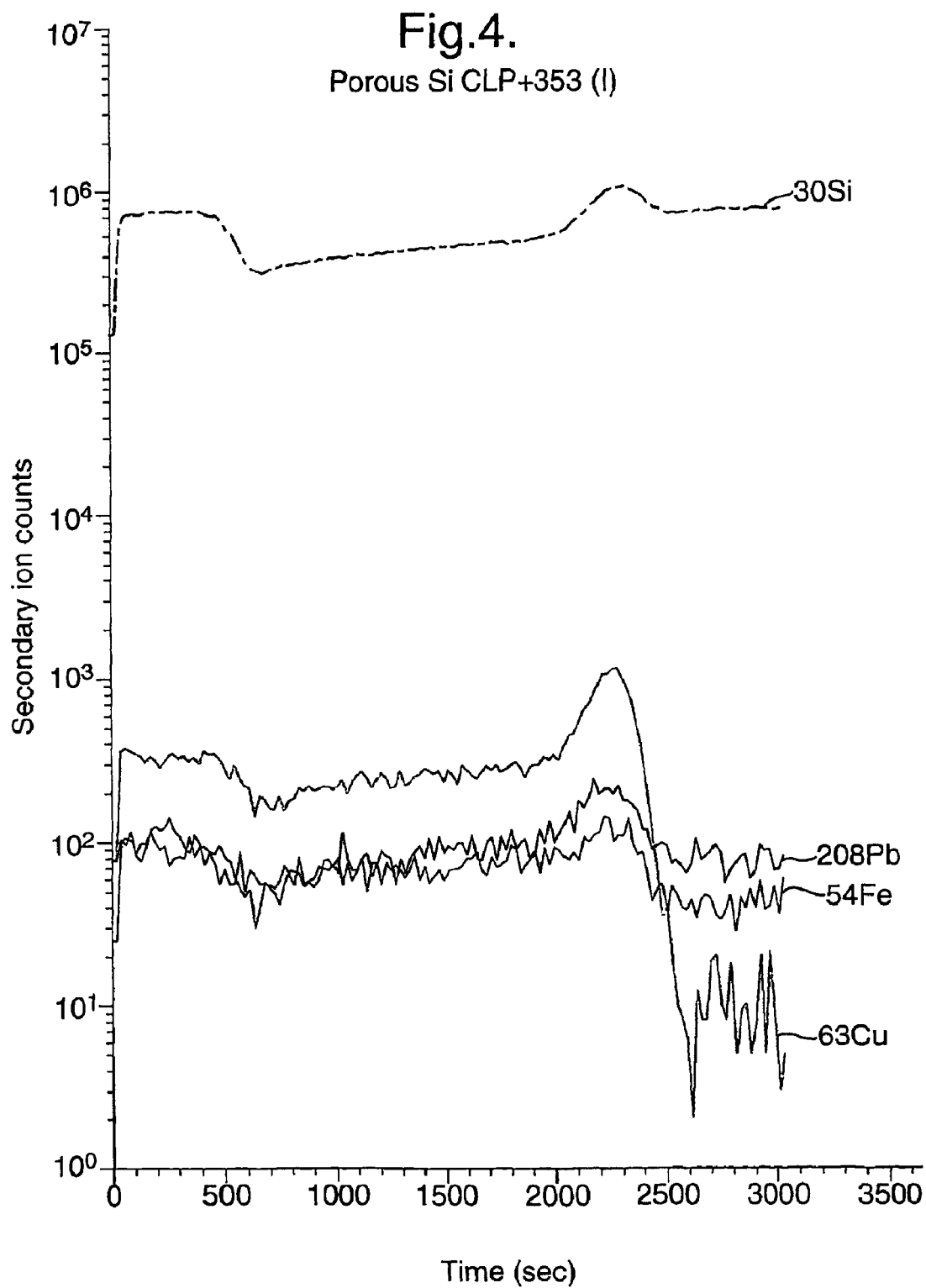

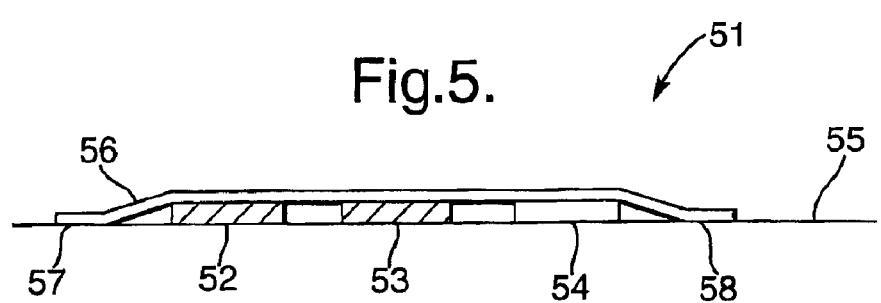
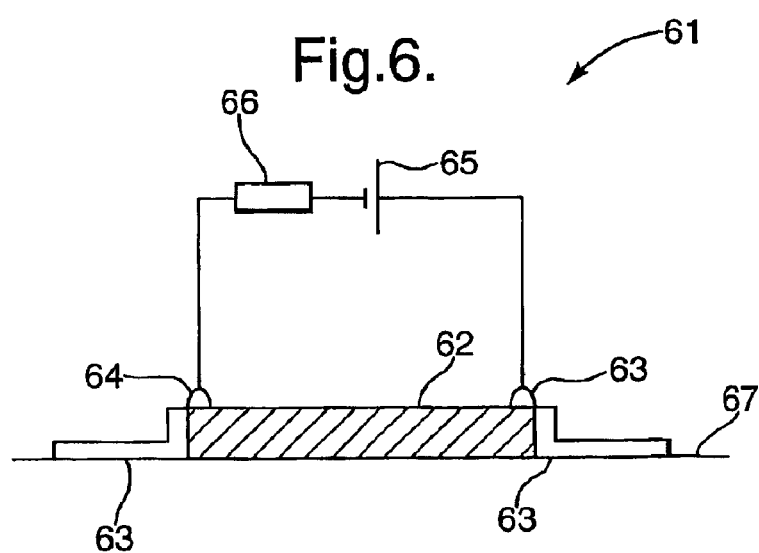
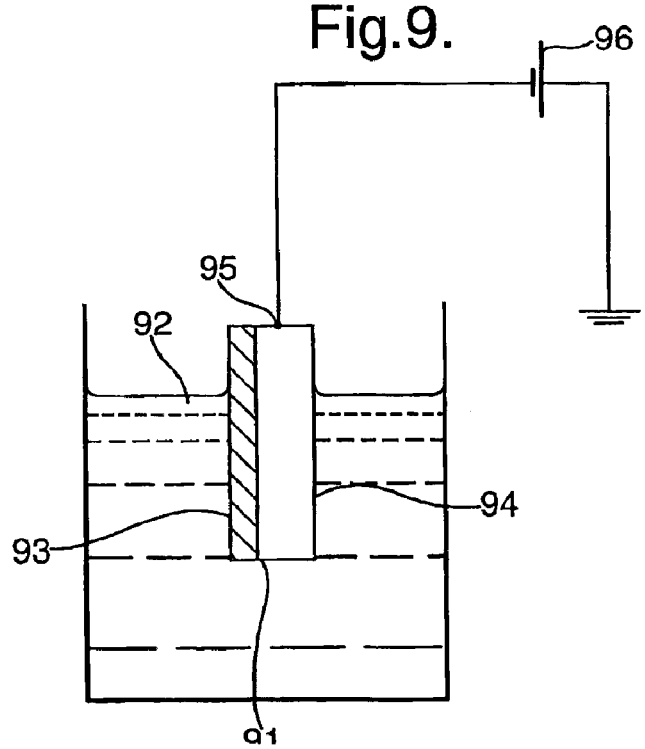

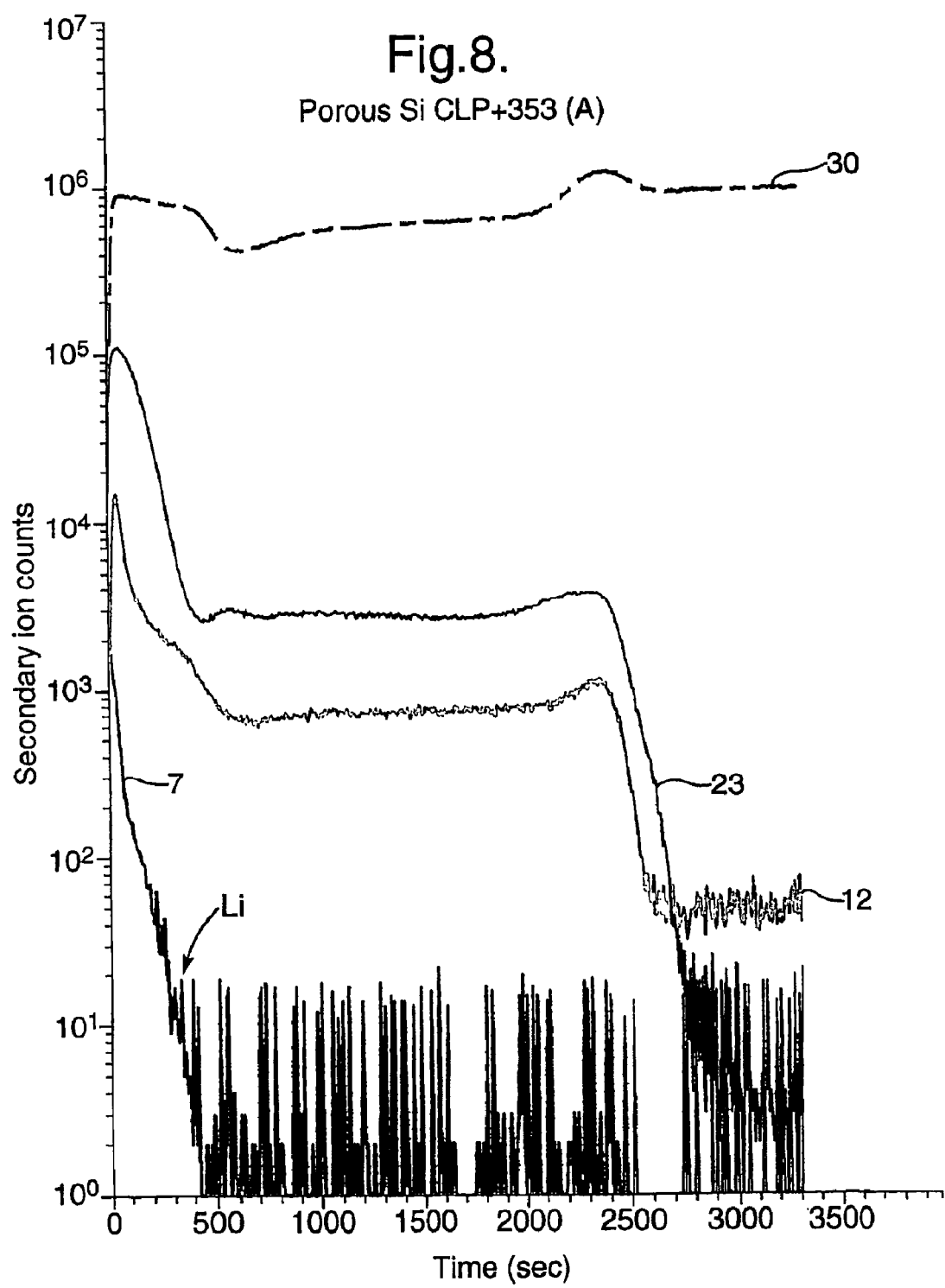

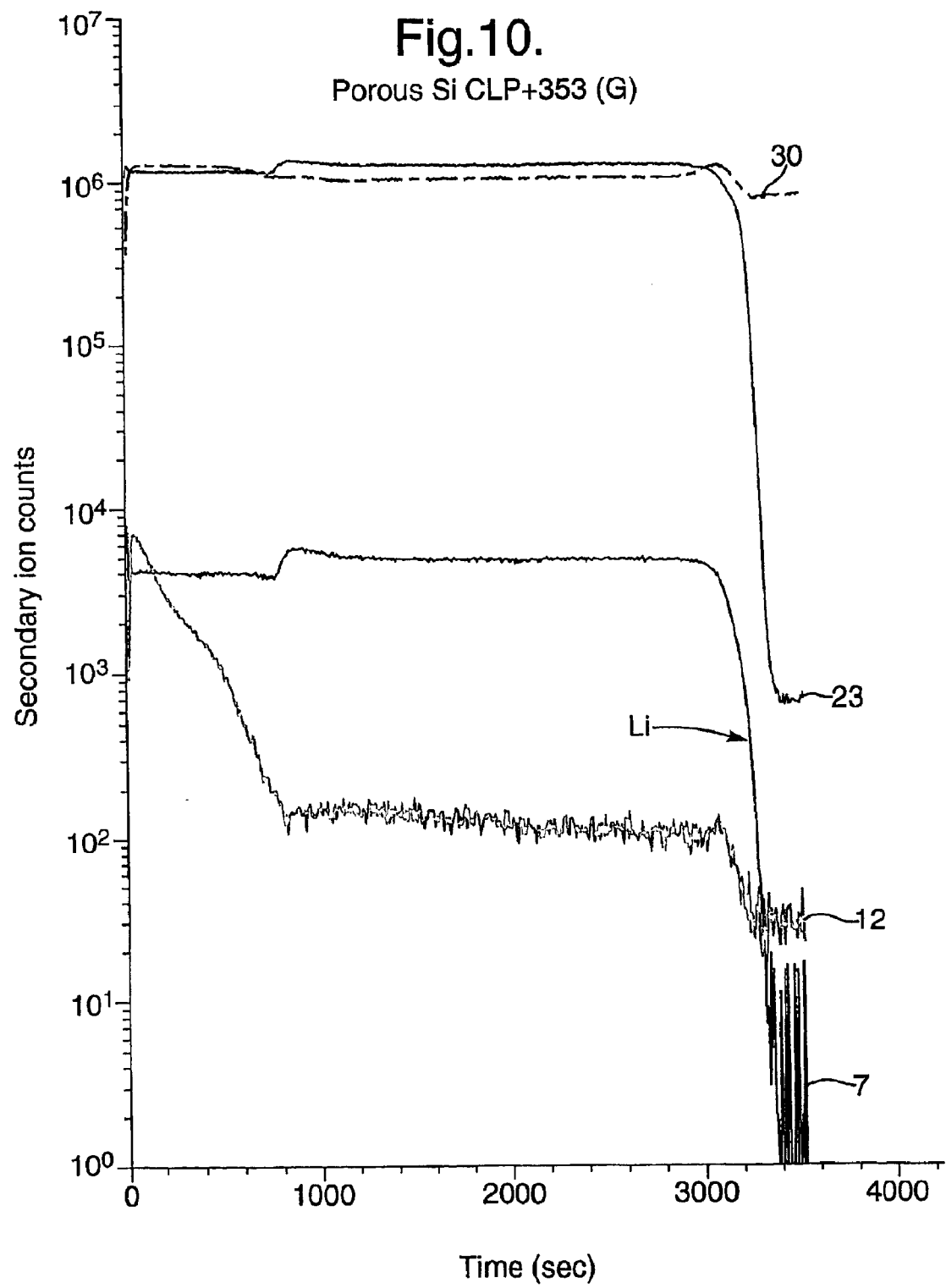

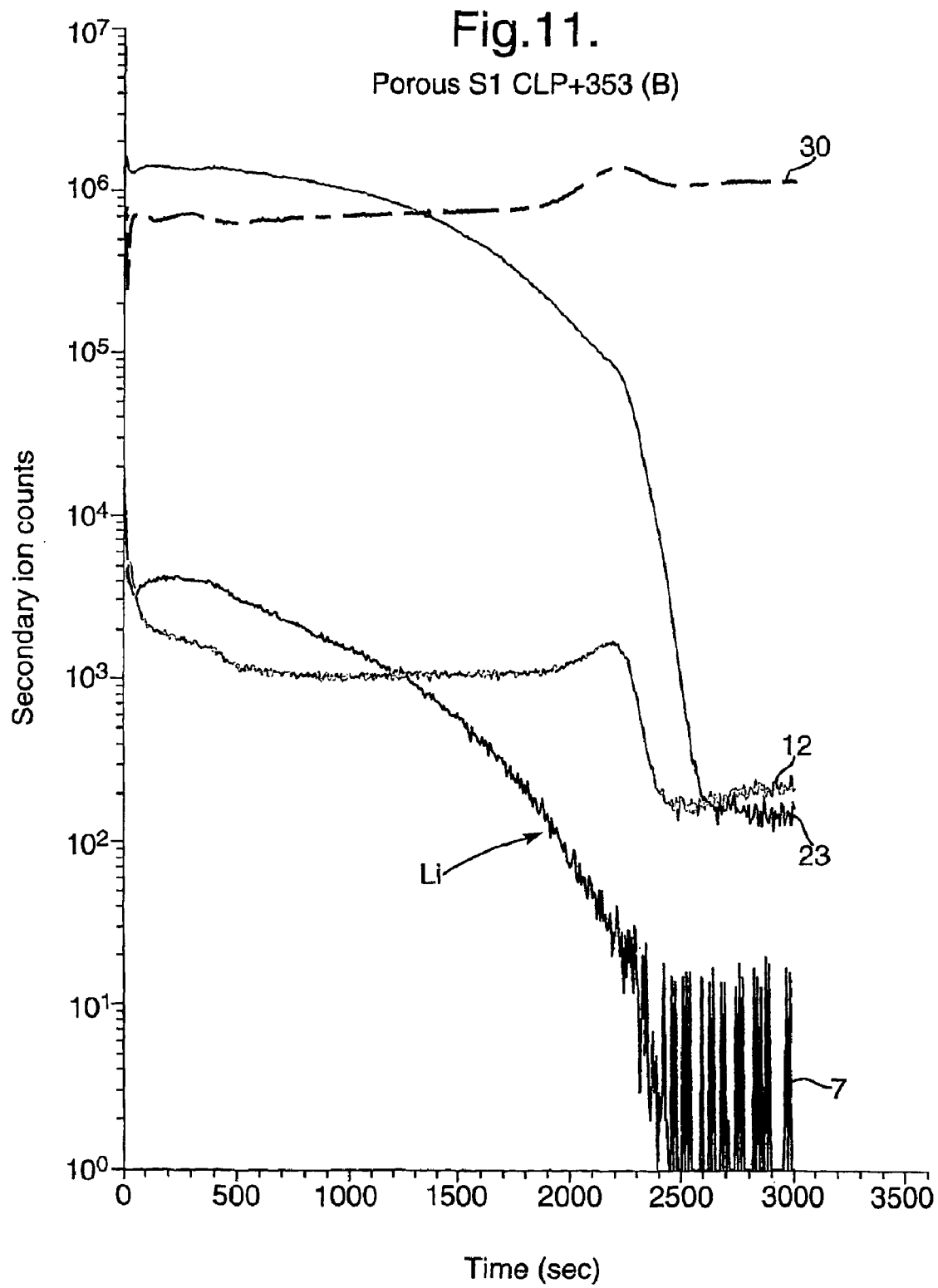

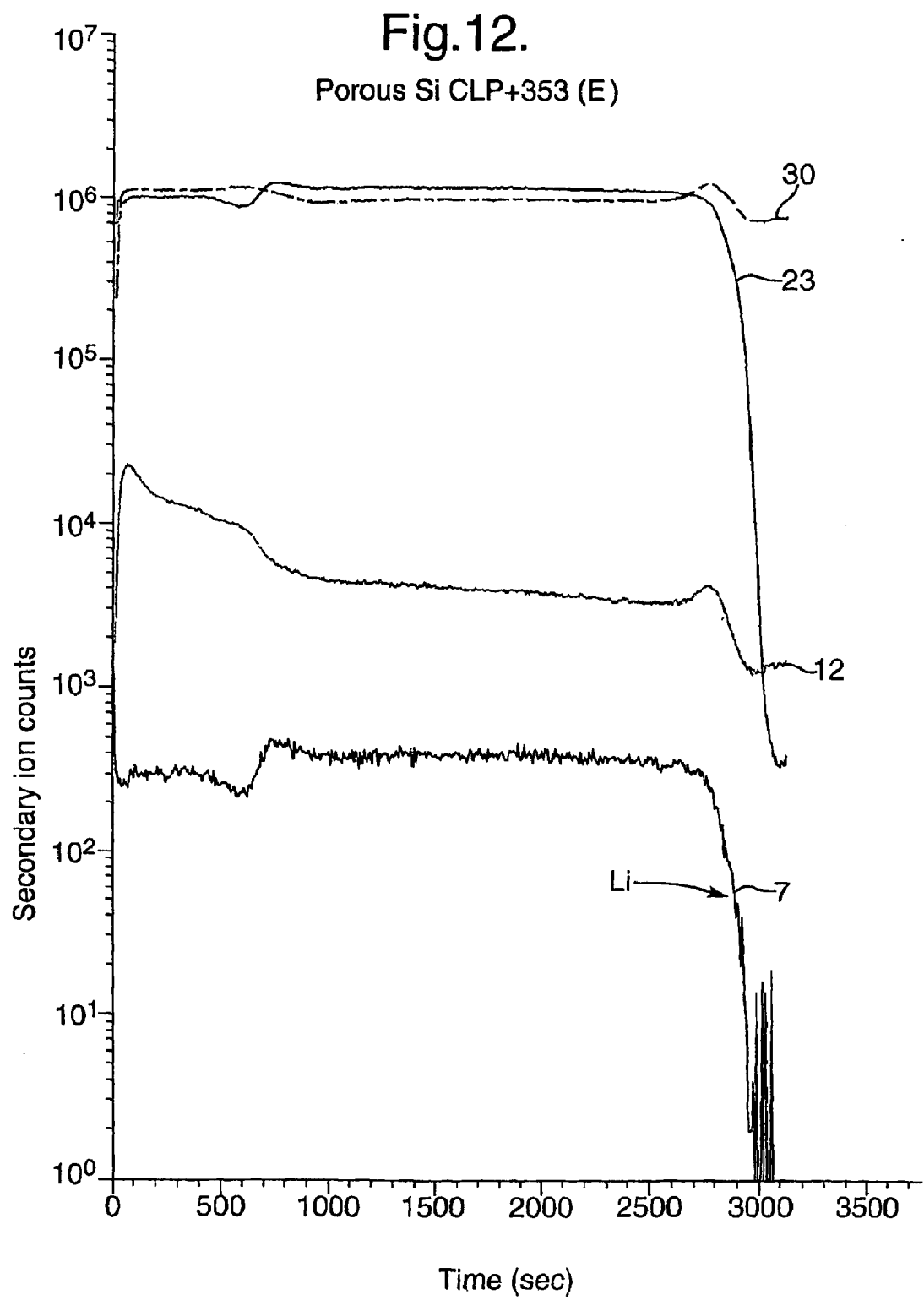

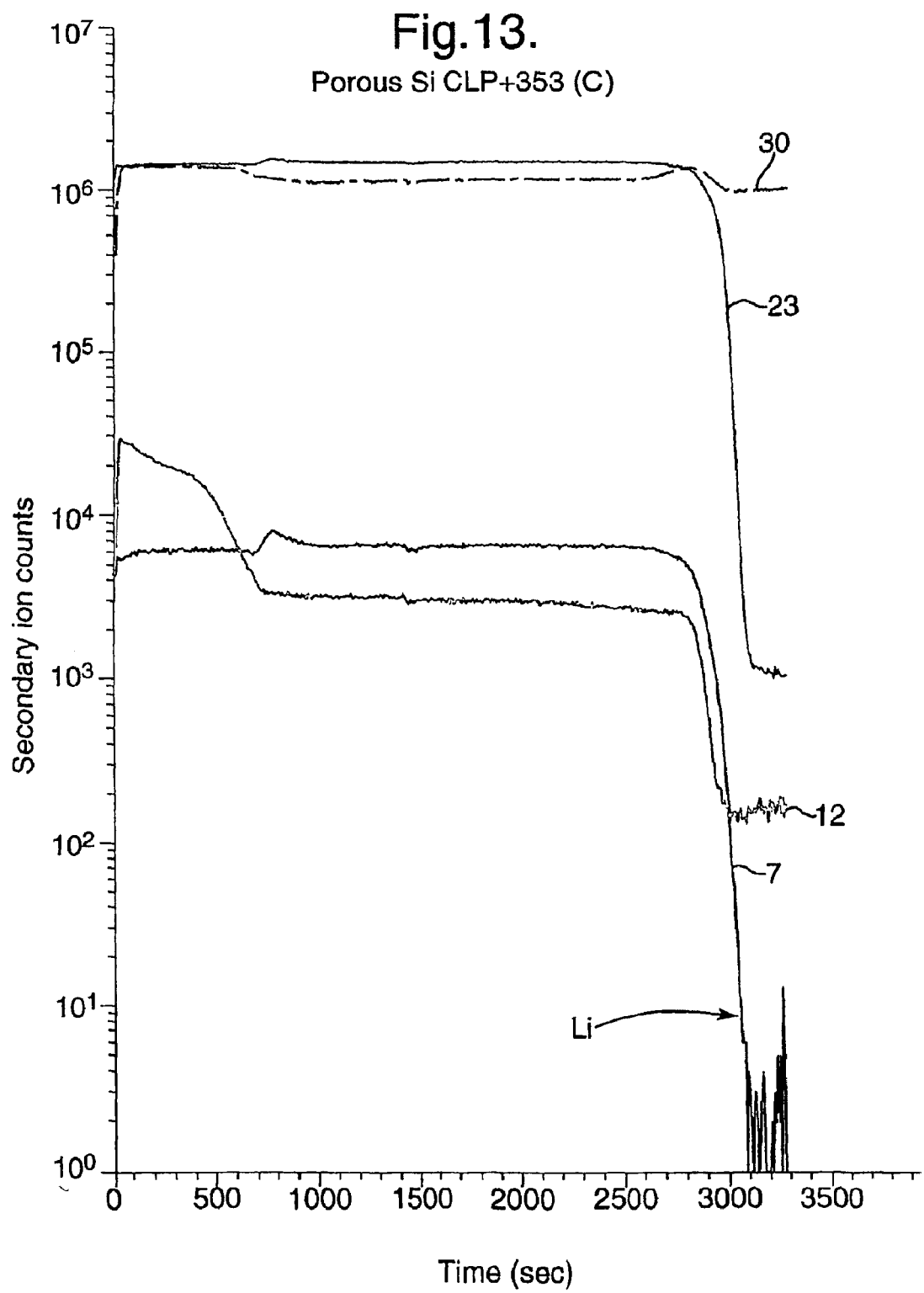

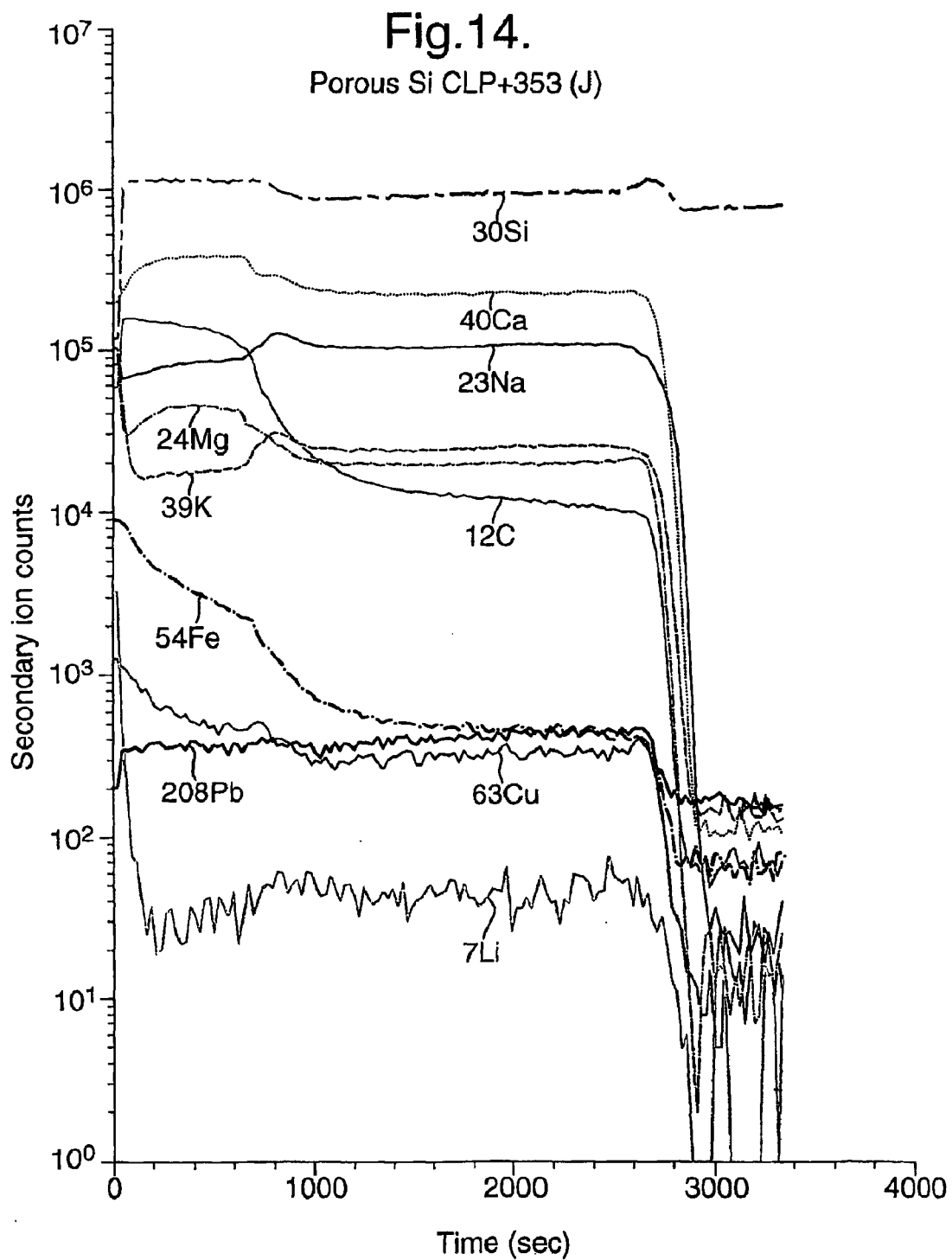

BODY FLUID COLLECTION AND ANALYSIS

This application is the U.S. national phase of international application PCT/GB02/03731 filed 14 Aug. 2002 which designated the U.S. and claims benefit of GB 0120202.7, dated 18 Aug. 2001, the entire content of each of which is hereby incorporated by reference.

BACKGROUND OF THE INVENTION

This invention relates to the collection of body fluids and to the analysis of body fluids. More specifically this invention relates to the collection of sweat and to the analysis of sweat.

The analysis of body fluids, of animals or humans, may be of value in the detection of disease, or substances, such as drugs, absorbed by a subject. Blood, saliva, urine, and sweat have all been used for such analysis. Although blood is the most commonly tested fluid, sweat probably provides the most inexpensive, safe, and convenient source of a number of analytes. Devices used to collect sweat, are commonly referred to as sweat patches.

In addition to water and electrolytes, sweat contains trace elements such as zinc, cadmium and lead. The trace elements found in sweat probably originate from blood serum. Labile metals can dissociate from proteins under the influence of the concentration gradient existing across blood capillaries, and diffuse through the capillary walls into the sweat glands.

Other substances that have been identified in sweat include: ascorbic acid, thiamine, riboflavin, nicotinic acid, amino acids, ethanol, antipyrine, creatinine, thiourea, lactate, theophylline, parathion, tetrahydrocannabinol, and insulin. Examples of disease that have been linked to the increased presence of a particular chemical in sweat include: pronounced uremia, leukaemia, and diabetes.

Typically a patch is used to collect the substance of interest, from the sweat of a person being tested. The patch is adhered to the skin of the person to be tested for a period of time, and sweat is absorbed into a fibrous pad. The pad is then analyzed for the substance.

An example of a prior art sweat patch, generally indicated by 11, is shown in FIG. 1. In addition to the storage means which comprises a fibrous pad 12, the patch comprises a semipermeable membrane 13 and a backing layer 14. The backing layer 14 is formed into a receptacle for the fibrous pad 12 and has an adhesive surface 15 for bonding the patch to the skin 16 of the patient or person being tested. The semipermeable membrane 13 separates the fibrous pad 12 from the dermal surface and may control which, and the rate at which, analytes enter the receptacle.

The design of sweat patches is a complex process. It is desirable that the environment of the skin under analysis be as little affected as possible by the presence of the patch. Sweating must occur or be made to occur in order to test the sweat. For quantitative analysis, it is desirable for the rate at which the analyte is collected to be relatively constant. The storage means used to collect the analyte should have a composition and construction such that an appropriate technique may be deployed for separation and analysis of the sweat contents. It is desirable that the storage means comprise a material that is reasonably stable when in contact with sweat.

The following documents each relate to part of the background to the present invention: U.S. Pat. No. 5,203,327; U.S. Pat. No. 4,756,314; GB 2,303,847 A; GB 2,324,866 A; and JP 10080266 A.

A number of different devices are described in U.S. Pat. No. 5,203,327. The Main theme common to these devices is the presence of a concentration zone that allows the concentration of a sweat component to be increased for testing.

The main problem addressed by U.S. Pat. No. 4,756,314 is the large variation in sweat uptake that may occur from individual to individual. The disclosure suggests that this variation may be reduced.

GB 2,303,847 A relates to bioactive silicon, resorbable silicon, and biocompatible silicon.

GB 2,324,866 A relates to an analytical device for analyzing biological materials such as blood and bile.

JP 10,080,266 A this document discloses equipment for immobilisation of a biopolymer or organism.

SUMMARY OF THE INVENTION

It is an objective of the present invention to address at least some of the above mentioned issues.

According to a first aspect, the invention provides an attachable body fluid collection device comprising at least one storage means for, when in use, storing a body fluid sample secreted by a body fluid secreting surface, characterised in that the or at least one of the storage means comprises silicon.

Preferably the silicon, from which the or at least one of the storage means is at least partly formed, comprises silicon that has been partially oxidized. More preferably the or at least one of the storage means comprises a storage sample of porous silicon, the sample of porous silicon being partially oxidized.

For the avoidance of doubt the term "partially oxidized" is used, in the specification, to describe a material that has been oxidized in such a manner that part of the material remains completely unoxidized. Therefore a sample of porous silicon that had been partially oxidized would comprise porous silicon in a completely unoxidized state.

Advantageously the silicon, from which the or at least one of the storage means is at least partly formed, comprises silicon that has been partially oxidized in such a manner that a monatomic layer of silicon is formed on at least part of the surface of the silicon. More advantageously the or at least one of the storage means comprises a storage sample of porous silicon, the sample of porous silicon being partially oxidized in such a manner that a monatomic layer of silicon is formed on at least part of the surface of the silicon.

The or at least one of the storage means comprises a storage sample of porous silicon, the sample of porous silicon being partially oxidized in such a manner that between 0.1% and 99% of the porous silicon atoms are bonded to oxygen. The or at least one of the storage means comprises a storage sample of porous silicon, the sample of porous silicon being partially oxidized in such a manner that between 0.1% and 10% of the porous silicon atoms are bonded to oxygen. The or at least one of the storage means comprises a storage sample of porous silicon, the sample of porous silicon being partially oxidized in such a manner that between 0.1% and 50% of the porous silicon atoms are bonded to oxygen.

The or at least one of the storage means may comprise silicon oxide. The or at least one of the storage means may comprise porous silicon oxide.

Advantageously the or at least one of the storage means comprises a storage sample of porous silicon that has been partially oxidized, the partially oxidized porous silicon having a structure and composition such that it is substantially un-corroded after contact with simulated human sweat for a period between 5 minute and 1 year.

More advantageously the or at least one of the storage means comprises a storage sample of porous silicon that has been partially oxidized, the partially oxidized porous silicon having a structure and composition such that it is substantially un-corroded after contact with simulated human sweat for a period between 5 minutes and 1 month.

Yet more advantageously the or at least one of the storage means comprises a storage sample of porous silicon that has been partially oxidized, the partially oxidized porous silicon having a structure and composition such that it is substantially un-corroded after contact with human sweat for a period between 10 minutes and 10 days.

Even more advantageously the or at least one of the storage means comprises a storage sample of porous silicon that has been partially oxidized, the partially oxidized porous silicon having a structure and composition such that it is substantially un-corroded after contact with human sweat for a period between 1 hour and 24 hours.

The or at least one of the storage means may comprise a silicon particulate product, the silicon particulate product comprising a multiplicity of silicon particles, each silicon particle comprising one or more of: bulk crystalline silicon, porous silicon, polycrystalline silicon, and amorphous silicon. At least some of the silicon particles may be partially oxidized.

The mean particle size of the silicon particulate product may be between 1 micron and 1 mm. The mean particle size of the silicon particulate product may be between 10 microns and 100 microns.

Once a sufficient quantity of the body fluid has been collected by the or at least one of the storage means, the sample of body fluid may be analyzed by a suitable analytical technique. The analysis may be performed in situ, or it may be performed after the collection is complete.

The collection device may further comprise an analytical means for analyzing at least part of the body fluid sample.

Preferably the attachable body fluid collection device further comprises an attachment means for attaching the or at least one of the storage means to part of a surface of an animal or human body. The attachment means may comprise a tape or sheet or fabric or plastic material. The attachment means may comprise an adhesive or flexible band or flexible garment. The garment may be designed to surround part of the animal or human body, for example the garment may be a glove or sleeve or cuff or head band or wrist band or arm band. The attachment means may comprise a solid object. The attachment means may be a ring, or necklace, or bracelet.

The silicon, from which the or at least one of the storage means is at least partly formed, may be selected from one or more of: porous silicon, polycrystalline silicon, amorphous silicon, bulk crystalline silicon, resorbable silicon, bioactive silicon, and biocompatible silicon.

For the purposes of this specification the term bioactive silicon is to be taken as silicon that is capable of forming a bond with living tissue. For the purposes of this specification the term resorbable silicon is to be taken as a form of silicon that is corrodible in a physiological liquid. For the purposes of this specification the term resorbable silicon is to be taken to include silicon that is resorbable in sweat. In other words the term resorbable silicon encompasses silicon that corrodes in sweat.

Preferably the silicon, from which the or at least one of the storage means is at least partly formed, comprises a storage sample of porous silicon. More preferably the storage sample of porous silicon has a structure such that the porous silicon is substantially un-corroded after contact with simulated human sweat for a period greater than or equal to 10 minutes. Yet more preferably the storage sample of porous silicon has a structure such that the storage sample is substantially un-corroded after contact with simulated human sweat for a period greater than or equal to 20 hours. Even more preferably the storage sample of porous silicon has a structure such that the storage sample is substantially un-corroded after contact with simulated human sweat for a period greater than or equal to 1 week.

Advantageously the storage sample of porous silicon has a porosity between 1% and 99%, more advantageously the storage sample of porous silicon has a porosity between 10% and 80%, even more advantageously the storage sample of porous silicon has a porosity between 10% and 60%.

The storage sample of porous silicon may comprise microporous silicon, having a pore diameter between 1.0 and 2.0 nm.

The storage sample of porous silicon may comprise mesoporous silicon, having a pore diameter between 2.0 and 50 nm.

The storage sample of porous silicon may comprise macroporous silicon, having a pore diameter between 50 nm and 5 microns.

Simulated human sweat is herein defined as an aqueous solution comprising NaCl (20 g/litre), NH4Cl (17.5 g/litre), urea (5 g/litre), acetic acid (2.5 g/litre), and lactic acid (15 g/litre).

This definition corresponds to that of ISO standard (3160/2), which is described by J P Randin in J Biomed Mater Res 22, 649 (1988).

The pH may be adjusted to 5.5 by the addition of NaOH.

The pH may be adjusted to 6.5 by the addition of NaOH.

The simulated human sweat may substantially consist of an aqueous solution of NaCl (20 g/litre), NH4Cl (17.5 g/litre), urea (5 g/litre), acetic acid (2.5 g/litre), and lactic acid (15 g/litre) and NaOH, the concentration of NaOH being such that the pH of the simulated human sweat is between 3.0 and 7.0.

The body fluid secreting surface may be an internal surface, found say in the mouth of an animal or human, or an external surface, such as the surface of skin of an animal or human.

The body fluid secreting surface may be skin, or a mucous membrane or a buccal membrane or a nipple. Preferably the body fluid is sweat, the body fluid sample being a sweat sample. Advantageously the body fluid collection device is a sweat patch.

The sweat sample may comprise a sweat element. The sweat sample may comprise a sweat compound.

For the absence of doubt the term "body fluid sample" is to be taken as a sample of one or more substances that may be found in a body fluid of an animal or human. Similarly the term "sweat sample" is to be taken as a sample of one or more substances that may be found in sweat.

The sweat sample may comprise a material selected from one of more of: a non-aqueous component of sweat, one or more organic compounds that may be found in sweat, one or more ionic compounds that may be found in sweat, and water.

The sweat sample may comprise a material selected from one or more of: ascorbic acid, thiamine, riboflavin, nicotinic acid, an amino acid, ethanol, antipyrine, creatinine, thiourea, lactate, theophylline, parathion, tetrahydrocannabinol, insulin, cimetidine, dimethylacetamide, fluorine, bromine, iron, bismuth, lactic acid, pyruvate glucose, ammonia, uric acid, nicotine, morphine, sulfanimide, atabrin, methadone, phencyclidine, aminopyrine, sulfadiacine, an amphetamine, benoylecgonine, phenobarbital, an androgen steroid, phenytoin, and carbamazepine.

The or at least one of the storage means may comprise a storage sample of porous silicon. The storage sample of porous silicon may have a structure and composition such that, when the storage sample of porous silicon is brought into contact with simulated human sweat for a period greater than 10 minutes a sweat element is detectable by secondary ion mass spectrometry, in or on at least part of the storage sample of porous silicon.

The or at least one of the storage means may comprise a storage sample of porous silicon that has been partially oxidized, the partially oxidized porous silicon having a structure and composition such that, when the storage sample of porous silicon is brought into contact with simulated human sweat for a period between 10 minutes and 48 hours, a sweat element is detectable by secondary ion mass spectrometry, in or on at least part of the partially oxidized sample of porous silicon.

The or at least one of the storage means may comprise a storage sample of porous silicon that has been partially oxidized, the partially oxidized porous silicon having a structure and composition such that, when the storage sample of porous silicon is brought into contact with human sweat for a period between 10 minutes and 48 hours, a sweat element is detectable by secondary ion mass spectrometry, in or on at least part of the partially oxidized sample of porous silicon.

For the purposes of this specification a sweat element is an element that may be found in sweat. The sweat element may be one or more of sodium, chlorine, potassium, calcium, magnesium, lead, cadmium, zinc, and lithium. The sweat element or elements may form part of a compound found in sweat.

The storage sample of porous silicon may have a structure and composition such that, when the porous silicon is brought into contact with a simulated human sweat for period greater than or equal to 10 minutes, a sweat element is detectable by secondary ion mass spectrometry, in or on at least part of the storage sample of porous silicon.

The storage sample of porous silicon may have a structure and composition such that, when the storage sample of porous silicon is brought into contact with simulated human sweat for a period greater than 10 minutes a sweat organic compound is detectable in or on at least part of the storage sample of porous silicon by a matrix assisted laser desorption ionisation (MALDI) technique.

The value of the MALDI technique in relation to the detection of biomolecules that are present on a sample of porous silicon is described in Nature Vol 399, p243–246 (1999).

The storage sample of porous silicon may be partially oxidized, the partially oxidized porous silicon having a structure and composition such that, when the partially oxidized porous silicon is brought into contact with simulated human sweat for a period between 5 minutes and 6 months, a sweat organic compound is detectable in or on at least part of the partially oxidized porous silicon by a matrix assisted laser desorption ionisation (MALDI) technique.

The storage sample of porous silicon may be partially oxidized, the partially oxidized porous silicon having a structure and composition such that, when the partially oxidized porous silicon is brought into contact with human sweat for a period between 5 minutes and 6 months, a sweat organic compound is detectable in or on at least part of the partially oxidized porous silicon by a matrix assisted laser desorption ionisation (MALDI) technique.

For the purposes of this specification, a sweat compound is a compound that may be found in sweat. A sweat compound may be a protein that may be found in sweat.

The use of a storage means comprising porous silicon may be advantageous since the porous silicon may perform a dual function of filtration and storage. The porous silicon in the region of the skin acting as a filter by, for example, preventing entry of skin cells into the part of the porous silicon to be analyzed, but allowing passage of the sweat sample. Porous silicon also opens the way for the use of biasing to assist with deposition of the body fluid sample on the storage means. It also allows the use of biasing to assist with the separation of the sweat sample prior to analysis of the sample.

The attachable fluid collection device may comprise a semi-permeable membrane. The semipermeable membrane may have a structure and composition such that it allows the passage, of at least one substance found in sweat, through the membrane. The semipermeable membrane may comprise porous silicon. The semipermeable membrane may comprise derivatized porous silicon. The semipermeable membrane may comprise porous silicon that has been partially oxidized. The or at least one of the storage means may be arranged such that it is in contact with the semipermeable membrane. The or at least one of the storage means and the semipermeable membrane may both be arranged such that they are in communication with each other, so that a sweat sample may pass from the semipermeable membrane to the or at least one of the storage means.

For the purposes of this specification, the term "derivatized porous silicon" should be taken as porous silicon having a covalently bound monolayer that has been formed on at least part of its surface. Examples of derivatized porous silicon, falling within this definition, are given in PCT/US99/01428.

The semipermeable membrane may comprise partially oxidized silicon. The semipermeable membrane may comprise partially oxidized porous silicon.

The storage sample of porous silicon and semipermeable membrane may both form part of a unitary sample of porous silicon. The storage sample of porous silicon and semipermeable membrane may both form part of a unitary sample of porous silicon that has been partially oxidized.

The unitary sample of porous silicon may have a low porosity small pore size layer, from which the semipermeable membrane is formed, connected to a high porosity layer, from which the storage sample is formed. The unitary sample of porous silicon may have a low porosity small pore size layer that has been partially oxidized, from which the semipermeable membrane is formed, connected to a high porosity layer that has been partially oxidized, from which the storage sample is formed.

The unitary sample of porous silicon may have a low porosity from which the semipermeable membrane is formed, connected to a high porosity layer, from which the storage sample is formed. The unitary sample of porous silicon may have a low porosity layer that has been partially oxidized, from which the semipermeable membrane is formed, connected to a high porosity layer that has been partially oxidized, from which the storage sample is formed.

The fluid collection means may comprise derivatized porous silicon. The derivatized porous silicon may comprise an organic compound, said organic compound comprising a carbon chain. For the purposes of this specification, derivatized porous silicon is to be taken as a type of porous silicon.

Derivatization may be selected to allow wetting of the or at least one of the storage means. Alternatively derivatization may be selected to enhance stability of the porous silicon against dissolution or corrosion by the body fluid. The derivatization may be such that the porous silicon selectively binds to one component, or a limited number of components, in the body fluid.

Preferably the silicon, from which the or at least one of the storage means is at least partly formed, comprises derivatized porous silicon. More preferably the derivatized porous silicon has a structure such that the derivatized porous silicon is substantially un-corroded after contact with simulated human sweat for a period greater than or equal to 10 minutes. Yet more preferably the derivatized porous silicon has a structure such that the derivatized porous silicon is substantially un-corroded after contact with simulated human sweat for a period greater than or equal to 1 day. Even more preferably the derivatized porous silicon has a structure such that the derivatized porous silicon is substantially un-corroded after contact with simulated human sweat for a period greater than or equal to 1 week.

The attachable collection device may further comprise a backing layer. The backing layer may be constructed in such a manner that it forms a receptacle for the or at least one of the storage means. At least part of the backing layer may form at least part of said attachment means. The backing member may be permeable or impermeable.

The backing layer may comprise silicon, the backing layer may comprise bulk crystalline silicon.

The backing layer may serve to isolate the collection means from the environment surrounding the attachable collection device, including neighbouring areas of skin. The backing layer may be permeable to allow water vapour to escape from the attachable collection device.

The ability of the storage sample of porous silicon to interact with, or generate, electromagnetic radiation, may be affected by contact with the sweat sample. Changes in such properties of porous silicon may be used to detect the presence of, or analyze elements and compounds found in sweat.

The or at least one of the storage means may comprise a storage sample of porous silicon having a structure and composition such that contact between the porous silicon and at least part of the sweat sample causes a change in one or more of: the photoluminescence efficiency, photoluminescence spectrum, the reflectivity, the absorbance, and the photoluminescence decay time of the porous silicon.

The or at least one of the storage means may comprise a storage sample of porous silicon, which has been partially oxidized, the partially oxidized porous silicon having a structure and composition such that contact between the partially oxidized porous silicon and at least part of the sweat sample causes a change in one or more of: the photoluminescence efficiency, photoluminescence spectrum, the reflectivity, the absorbance, and the photoluminescence decay time of the partially oxidized porous silicon.

The body fluid collection device may comprise at least one reference storage means and at least one derivatized storage means. The or each reference storage means comprising silicon. The or each derivatized storage means comprising derivatized silicon, the derivatization being selected such that, when brought into contact with sweat, the derivatized silicon binds to a sweat element or sweat compound or part of a sweat compound. Preferably the derivatization is such that the derivatized porous silicon may bond covalently with a sweat element or part of a compound when brought into contact with sweat containing said element or compound.

The use of reference and derivatized storage means may be advantageous. Analysis of both the reference and derivatized storage means may allow comparison of the two types of storage means to determine whether binding to the sweat element or compound has occurred.

The body fluid collection device may comprise an electronic circuit. The body fluid collection means may comprise a means for determining the conductivity of the sweat sample. The body fluid collection device may comprise a means for monitoring the electrical impedance of at least part of the silicon from which the or at least one of the storage means is formed. The body fluid collection device may comprise a biasing means, for applying a potential difference across at least part of the silicon from which the or at least one of the storage means is formed, and a means for measuring the current density resulting from said potential difference.

The body fluid collection means may comprise at least one first storage means and at least one second storage means. The or at least one of said first storage means may comprise a first type of derivatized silicon, which is derivatized in such a manner that, when brought into contact with sweat, the first type of derivatized silicon binds to a first sweat element or compound. The or at least one of said second storage means may comprise a second type of derivatized silicon, which is derivatized in such a manner that, when brought into contact with sweat, the second type of derivatized silicon binds to a second sweat element or compound.

The use of two types of derivatization allows the detection of more than one element or compound found in sweat. A medical condition or presence of drug in a subject may be indicated by the presence of more than one element or compound in the sweat of the subject. Measurement of the relative concentrations of the elements or compounds in the sweat may also provide useful information.

According to a second aspect, the invention provides a method of collecting a body fluid sample from an animal or human comprising the steps:

(i) placing a silicon sample in fluid communication with part of a body fluid secreting surface of the animal or human;

(ii) allowing or causing the animal or human to express the body fluid sample; and (iii) collecting the body fluid sample on or in at least part of the silicon sample.

The method of collecting a body fluid sample may be a method of collecting and analyzing a body fluid sample, wherein the method further comprises the step (iv) of analyzing the body fluid sample that has been collected on or in at least part of the silicon sample.

The step (i) may comprise the step of placing a silicon sample that has been partially oxidized in fluid communication with part of a body fluid secreting surface of the animal or human, and the step (iii) may comprise the step of collecting the body fluid sample on or in at least part of the silicon sample that has been partially oxidized.

Preferably the body fluid sample is a sweat sample and step (i) comprises the step of (a) placing a silicon sample in fluid communication with part of the skin of the animal or human; step (ii) comprises the step of (b) allowing or causing the animal or person to express the sweat sample by sweating; step (iii) comprises the step of (c) collecting the sweat sample on or in at least part of the silicon sample.

The step (iv) of analyzing the body fluid sample may comprise the step (d) of analyzing the sweat sample that has been collected on or in at least part of the silicon sample.

The step of (iv) of analyzing the body fluid sample may comprise the step of detecting a body fluid sample, that has been collected on or in at least part of the silicon sample, by one of the following techniques: MALDI, SIMS, measurement of photoluminescence efficiency, measurement of photoluminescence spectra, reflectivity spectroscopy, absorbance spectroscopy, and measurement of photoluminescence decay time.

The step of analyzing the sweat sample may be performed after step (c) or it may be performed during at least part of step (c).

The step of analyzing the sweat sample may be performed while the sweat sample is in contact with at least part of the silicon sample.

The method may further comprise the step, which may be performed after step (c) and before the analysis step (d), of separating the sweat sample from the silicon sample.

The silicon sample may comprise one or more of: porous silicon, polycrystalline silicon, amorphous silicon, bulk crystalline silicon, bioactive silicon, resorbable silicon, biocompatible silicon, and derivatized porous silicon.

The silicon sample may comprise porous silicon that has been partially oxidized.

Preferably the silicon sample comprises a storage sample of derivatized porous silicon and step (c) comprises the step of collecting the sweat sample over a period of less than or equal to than 10 minutes, and allowing the storage sample of derivatized porous silicon to be substantially uncorroded during the collection period. Preferably the silicon sample comprises a storage sample of derivatized porous silicon and step (c) comprises the step of collecting the sweat sample over a period of less than or equal to than 20 hours, and allowing the storage sample of derivatized porous silicon to be substantially uncorroded during the collection period. Preferably the silicon sample comprises a storage sample of derivatized porous silicon and step (c) comprises the step of collecting the sweat sample over a period of less than or equal to than 1 week, and allowing the storage sample of derivatized porous silicon to be substantially uncorroded during the collection period.

Preferably the silicon sample comprises a storage sample of porous silicon and step (c) comprises the step of collecting the sweat sample over a period of less than or equal to than 10 minutes, and allowing the storage sample of porous silicon to be substantially uncorroded during the collection period. Preferably the silicon sample comprises a storage sample of porous silicon and step (c) comprises the step of collecting the sweat sample over a period of less than or equal to than 20 hours, and allowing the storage sample of porous silicon to be substantially uncorroded during the collection period. Preferably the silicon sample comprises a storage sample of porous silicon and step (c) comprises the step of collecting the sweat sample over a period of less than or equal to than 1 week, and allowing the storage sample of porous silicon to be substantially uncorroded during the collection period.

Step (a) may comprise the step of bringing a storage sample of porous silicon into contact with the skin of a human or animal for a period of greater than or equal to 10 minutes so that a sweat element is collected in or on at least part of the storage sample of porous silicon, and step (c) may comprise the step of detecting the sweat element, which has been deposited on at least part of the sample of porous silicon, by secondary ion mass spectrometry.

Step (a) may comprise the step of bringing a storage sample of porous silicon into contact with a sweat sample for a period of greater then or equal to 10 minutes so that a sweat organic molecule is collected in or on at least part of the storage sample of porous silicon, and step (c) may comprise the step of detecting the sweat organic molecule, that has been deposited on at least part of the sample of porous silicon, by a MALDI technique.

Step (a) may comprise the step of bringing a storage sample of porous silicon into contact with a sweat sample, and step of analyzing the sweat sample may comprise the step of monitoring a change in one or more of: the photoluminescence efficiency, photoluminescence spectrum, the reflectivity, the absorbance, and the photoluminescence decay time of at least part of the storage sample of porous silicon, said change resulting from the contact with the sweat sample.

The step (c) may comprise the step of applying a bias to the silicon sample in such a manner that the rate of collection of the sweat sample is accelerated, relative to the rate of deposition when the silicon sample is at earth potential. The step (c) may comprise the step of applying a bias to the porous silicon in such a manner that the rate of deposition of the sweat sample on the silicon is accelerated, relative to the rate of deposition when the silicon sample is at earth potential.

The step of separating the sweat sample from the silicon sample, prior to the analysis step, may comprise the step of immersing at least part of the silicon sample in a solvent. The step of separating the sweat sample from the silicon sample, when it is at least partly immersed in the solvent, may further comprise the step of applying a bias to the silicon sample in such a manner that the bias increases the rate at which the sweat sample moves from the silicon sample into the solvent, relative to the rate when the silicon sample is at earth potential.

The solvent may comprise one or more of water, ethanol, and acetone. The solvent may comprise any organic compound that is a liquid at 20 C. and a pressure of 760 mm Hg.

According to a third aspect the invention provides a use of a sample of silicon in the preparation of a medicament for collecting and analyzing, or for collecting and subsequently releasing for analysis, a body fluid sample from an animal or human.

The term "medicament" as used herein refers to any substance used in therapy or diagnosis.

The body fluid sample may be a sweat sample. Preferably the step of collecting the body fluid sample from the animal or human comprises the step of collecting a sweat sample from part of the skin of an animal or human.

The step of analyzing may comprise the step of detecting a sweat sample, that has been collected on or in at least part of the sample of silicon, by one of the following techniques: MALDI, SIMS, measurement of photoluminescence efficiency, measurement of photoluminescence spectra, reflectivity spectroscopy, absorbance spectroscopy, and measurement of photoluminescence decay time.

The step of releasing for analysis may comprise the step of releasing a sweat sample, that has been collected on or in at least part of the sample of silicon, for detection by one of the following techniques: MALDI, SIMS, photoluminescence spectroscopy, reflectivity spectroscopy, absorbance spectroscopy, and fluorescence spectroscopy.

The step of releasing for analysis may comprise the step of at least partly immersing the sample of silicon in a solvent so that the body fluid sample passes from the sample of silicon into the solvent.

The step of collecting the body fluid sample may comprise the step of increasing the rate of collection, relative to the rate of collection when the sample of silicon is at earth potential, by applying a bias to the sample of silicon.

The step of releasing the sample for analysis may comprise the step of increasing the rate of release, relative to the rate of release when the sample of silicon is at earth potential, by applying a bias to the sample of silicon.

The sample of silicon may comprise one or more of: porous silicon, polycrystalline silicon, amorphous silicon, bulk crystalline silicon, bioactive silicon, resorbable silicon, biocompatible silicon, and derivatized porous silicon.

The sample of silicon may comprise partially oxidized silicon. The sample of silicon may comprise partially oxidized porous silicon.

Preferably the sample of silicon comprises a storage sample of porous silicon and step of collecting the body fluid sample comprises the step of collecting a sweat sample over a period of less than or equal to than 10 minutes, and allowing the storage sample of porous silicon to be substantially uncorroded during the collection period. Preferably the sample of silicon comprises a storage sample of porous silicon and step of collecting the body fluid sample comprises the step of collecting a sweat sample over a period of less than or equal to than 20 hours, and allowing the storage sample of porous silicon to be substantially uncorroded during the collection period. Preferably the sample of silicon comprises a storage sample of porous silicon and step of collecting the body fluid sample comprises the step of collecting a sweat sample over a period of less than or equal to than 1 week, and allowing the storage sample of porous silicon to be substantially uncorroded during the collection period.

Advantageously the sample of silicon comprises a storage sample of partially oxidized porous silicon and step of collecting the body fluid sample comprises the step of collecting a sweat sample over a period of less than or equal to than 10 minutes, and allowing the storage sample of partially oxidized porous silicon to be substantially uncorroded during the collection period. Preferably the sample of silicon comprises a storage sample of partially oxidized porous silicon and step of collecting the body fluid sample comprises the step of collecting a sweat sample over a period of less than or equal to than 20 hours, and allowing the storage sample of partially oxidized porous silicon to be substantially uncorroded during the collection period. Preferably the sample of silicon comprises a storage sample of partially oxidized porous silicon and step of collecting the body fluid sample comprises the step of collecting a sweat sample over a period of less than or equal to than 1 week, and allowing the storage sample of partially oxidized porous silicon to be substantially uncorroded during the collection period.

The sweat sample may comprise a material selected from one of more of: a non-aqueous component of sweat, one or more organic compounds that may be found in sweat, one or more ionic compounds that may be found in sweat, and water.

The sweat sample may comprise a material selected from one or more of: ascorbic acid, thiamine, riboflavin, nicotinic acid, an amino acid, ethanol, antipyrine, creatinine, thiourea, lactate, theophylline, parathion, tetrahydrocannabinol, insulin, cimetidine, dimethylacetamide, fluorine, bromine, iron, bismuth, lactic acid, pyruvate glucose, ammonia, uric acid, nicotine, morphine, sulfanimide, atabrin, methadone, phencyclidine, aminopyrine, sulfadiacine, an amphetamine, benoylecgonine, phenobarbital, an androgen steroid, phenytoin, and carbamazepine.

According to a fourth aspect, the invention provides an attachable body fluid collection device comprising at least one storage means for, when in use, storing a body fluid sample secreted by a body fluid secreting surface, characterised in that the or at least one of the storage means comprises silicon oxide.

Preferably the silicon oxide has the chemical formula SiOx where $0.1 \leq x \leq 2$.

Advantageously the silicon oxide is porous silicon oxide, more advantageously the porous silicon oxide is integral with a substrate. The substrate may comprise one or more of: bulk crystalline silicon, silicon oxide, or partially oxidized bulk crystalline silicon.

According to a fifth aspect, the invention provides a method of collecting a body fluid sample from an animal or human comprising the steps:

(i) placing a silicon oxide sample in fluid communication with part of a body fluid secreting surface of the animal or human;

(ii) allowing or causing the animal or human to express the body fluid sample; and (iii) collecting the body fluid sample on or in at least part of the silicon oxide sample.

Advantageously the silicon oxide is porous silicon oxide, more advantageously the porous silicon oxide is integral with a substrate. The substrate may comprise one or more of: bulk crystalline silicon, silicon oxide, or partially oxidized bulk crystalline silicon.

According to a sixth aspect the invention provides a use of a sample of silicon oxide in the preparation of a medicament for collecting and analyzing, or for collecting and subsequently releasing for analysis, a body fluid sample from an animal or human.

Advantageously the silicon oxide is porous silicon oxide, more advantageously the porous silicon oxide is integral with a substrate. The substrate may comprise one or more of: bulk crystalline silicon, silicon oxide, or partially oxidized bulk crystalline silicon.

BRIEF DESCRIPTION OF THE DRAWINGS

The invention will now be described by way of example only with reference to the following drawings, in which:

FIG. 3 shows SIMS depth profiles for a number of sweat elements, the SIMS measurements being performed on the porous silicon sample represented in FIG. 2b, prior to contact with sweat;

FIG. 4 shows SIMS depth profiles for a further group of sweat elements, the SIMS measurements being performed on the FIG. 2b porous silicon sample, prior to contact with sweat;

FIG. 5 shows a schematic diagram of a body fluid collection device, according to the invention, comprising three body fluid storage means;

FIG. 6 shows a schematic diagram of a body fluid collection device, according to the invention, comprising a means for monitoring the resistance of a storage sample of porous silicon;

FIG. 8 shows a SIMS profile for a second storage sample of porous silicon, the image shows the effect of immersion in simulated sweat containing lithium ions;

FIG. 9 shows an apparatus to determine the behaviour of a storage sample of porous silicon, under an electrical bias, in simulated human sweat;

FIG. 10 shows a SIMS profile for a second storage sample of porous silicon and to which an anodic electric bias has been applied, the image shows the effect of immersion in simulated sweat containing lithium ions;

FIG. 11 shows a SIMS profile for a second storage sample of porous silicon and to which an cathodic electric bias has been applied, the image shows the effect of immersion in simulated sweat containing lithium ions;

FIG. 12 shows a SIMS profile for a fifth storage sample of porous silicon that has been partially oxidized, the image shows the effect of immersion in simulated sweat containing lithium ions;

FIG. 13 shows a SIMS profile for a fifth storage sample of porous silicon that has been partially oxidized, the image shows the effect of immersion in simulated sweat containing lithium ions; and FIG. 14 shows a SIMS profile for a fifth storage sample of porous silicon that has been partially oxidized, the image shows the effect of contact with human skin.

DESCRIPTION OF PREFERRED EMBODIMENTS

Structure, Composition, and Fabrication

Figure 1:
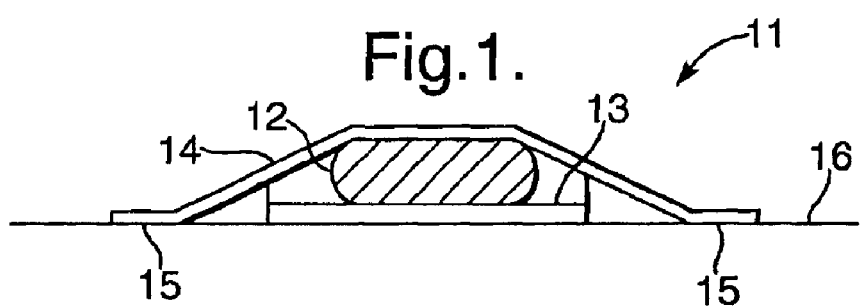
FIG. 1 is a schematic diagram of a prior art sweat patch.
Figure 2A:
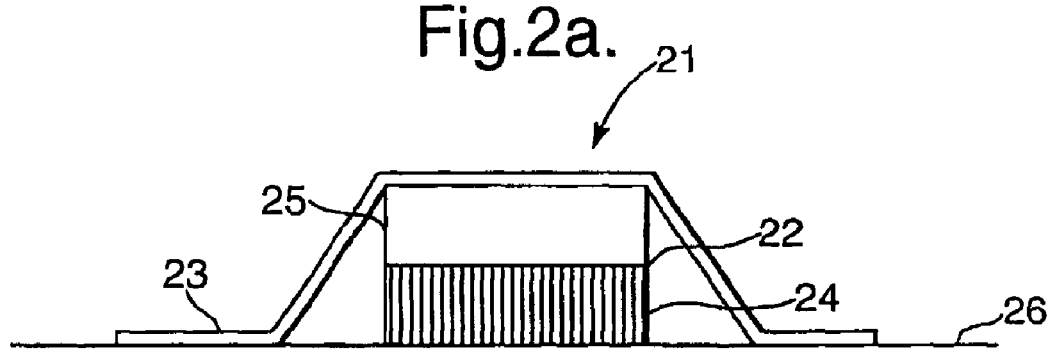
FIG. 2a is a schematic diagram of an attachable body fluid collection device according to the invention.

FIG. 2a shows a schematic diagram of an attachable body fluid collection device, generally indicated by 21, according to the invention. The fluid collection device 21 comprises a storage means 22, and an attachment means 23. The storage means comprises a first storage sample of porous silicon 24, and a portion of bulk crystalline silicon 25. The first storage sample of porous silicon 24 may comprise derivatized porous silicon.

The first storage sample of porous silicon may be prepared by a method, which will be referred to as "method A", which comprises the step of anodising bulk crystalline silicon by a standard technique such as that described in U.S. Pat. No. 5,348,618. The resulting first storage sample of porous silicon 24 is connected to the remaining portion of bulk crystalline silicon 25. The attachment means 23 holds the storage means in contact with a body fluid secreting surface, which in this case is human skin 26. The attachment means 23 may, for example, be an adhesive tape, the adhesive being present on only one side of the tape.

Any reference, in this specification, to a "first storage sample of porous silicon" should be taken as a reference to a storage sample of porous silicon prepared by method A.

Figure 2B:
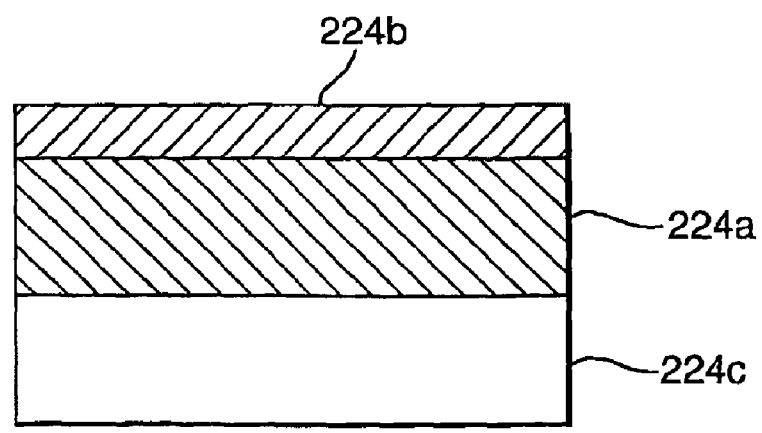
FIG. 2b is a schematic diagram of a storage sample of porous silicon that may form part of a body fluid collection device according to the invention.
Figure 7A:
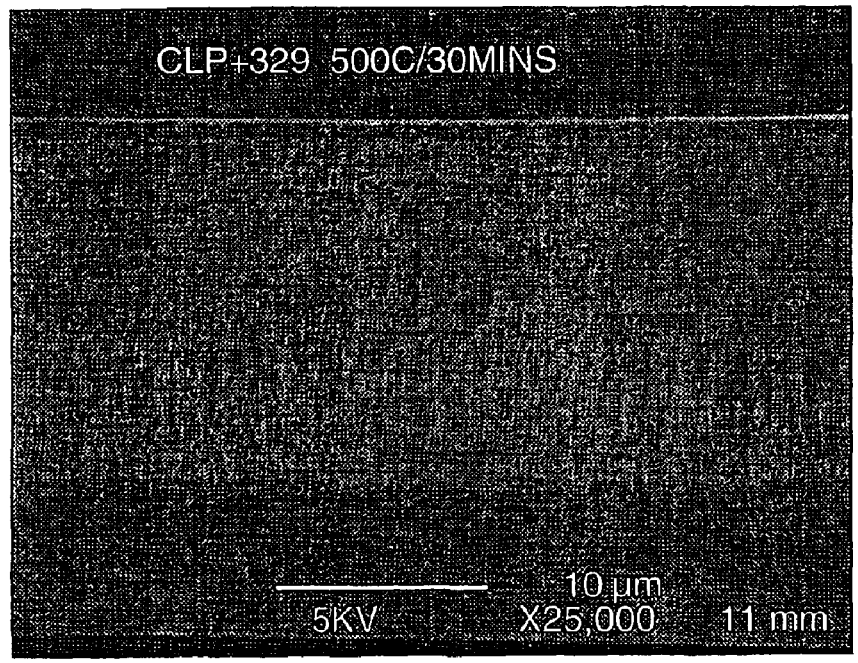
FIG. 7 shows SEM images of a third storage sample of porous silicon that has been partially oxidized and for a fourth storage sample of porous silicon that is un-oxidized, the images shows the effect of immersion in simulated sweat for these two samples of porous silicon.
Figure 7B:
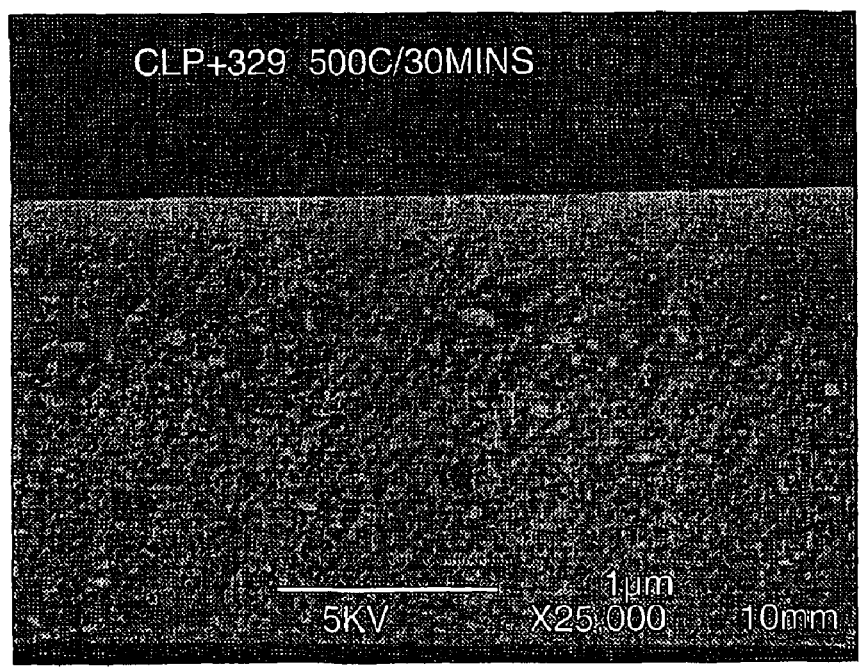
Figure 7C:
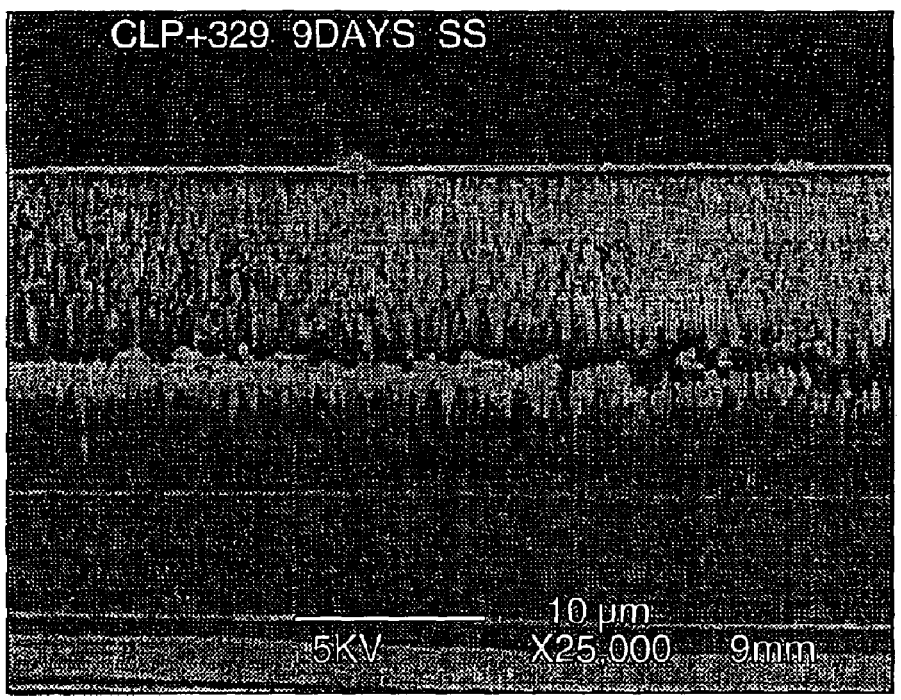
Figure 7D:
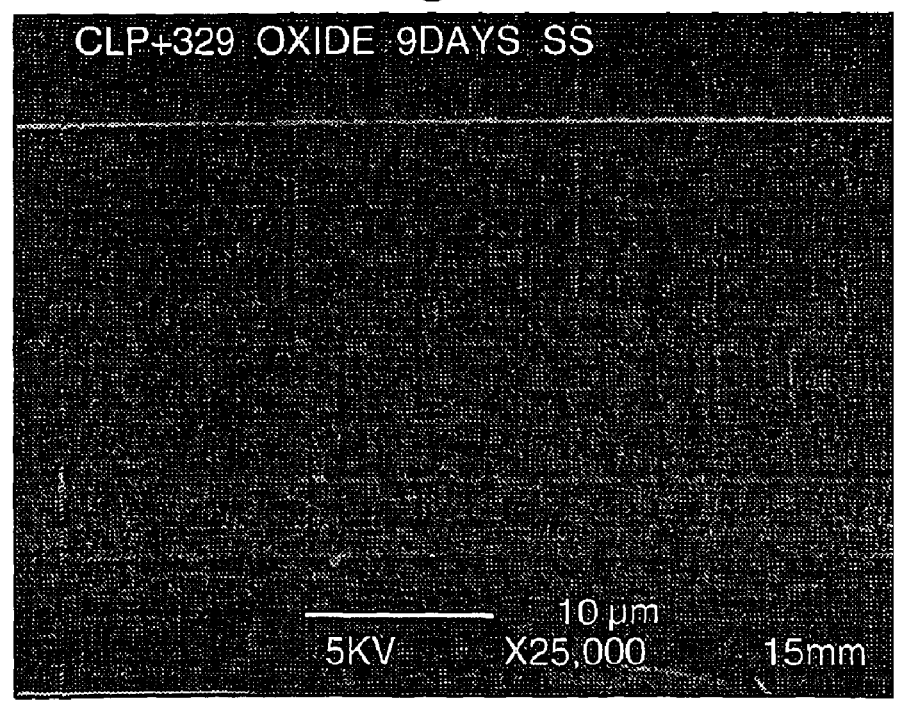

FIG. 2b shows a schematic diagram of a second storage sample of porous silicon 224a. The second storage sample of porous silicon was fabricated by the following method, which will be referred to as "method B":

A 0.005 ohm cm p+ wafer was anodised in 20% ethanoic HF. A current density of 5 mA cm$^{-2}$ was passed for 120 seconds, immediately followed by a current density of 50 mA cm$^{-2}$ for 120 seconds.

The application of two consecutive current densities in this way generated two layers 224a, 224b of porous silicon, one having a high porosity 224a, which forms the second storage sample of porous silicon 224a, and the other having low porosity 224b, which forms a semipermeable membrane. The low and high porosity layers 224a and 224b are connected to each other. The porosity of the second storage sample of porous silicon 224a, which is connected to the bulk crystalline substrate 224c, is 67%. The porosity of the semipermeable membrane 224b is 43%.

A storage sample of porous silicon prepared by method B will be referred to, in this specification, as a "second storage sample of porous silicon".

The low porosity semipermeable membrane 224b could be used to prevent dermal detritus reaching the higher porosity second storage sample of porous silicon 224a used to store the sweat sample.

FIG. 3 shows the SIMS depth profiles for the sweat elements: sodium, potassium, and lithium in the second storage sample of porous silicon, prior to exposure to sweat. Trace sodium is present throughout the layer at parts per million levels, this is indicated by the abrupt change in level with sputtering time as the sputtered region passes from the porous layer 224a into the underlying bulk crystalline substrate 224c. The results for sodium contrast with those for potassium and lithium, which are at the limits of detection by this technique, no corresponding change in signal level between the porous and bulk regions being observed for these two elements.

FIG. 4 shows SIMS depth profiles for three sweat elements: iron, lead, and copper in the second storage sample of porous silicon 224a prior to exposure to sweat. Copper is detectable at levels of the order of parts per million, whilst iron and lead are undetectable.

FIGS. 3 and 4 both show a SIMS depth profile for silicon. The variation of the SIMS signal with sputtering time provides an indication of the boundaries of the porous silicon layers. The signal resulting from silicon is present in all of the SIMS results presented in this patent application.

A Body Fluid Collection Device Comprising Three Storage Means

FIG. 5 shows a schematic diagram of a body fluid collection device, generally indicated by 51, according to the invention. The collection device 51 comprises a type x storage means 52, a type y storage means 53, and a type z storage means 54. Each storage means comprises porous silicon. The three storage means are in contact with the surface of the skin 55 of a subject. The storage means are attached by means of an attachment means 66 having adhesive surfaces 57 and 58. The type x storage means 52 may comprise type x derivatized porous silicon, the type y storage means 53 may comprise type y derivatized porous silicon, and the type z storage means 54 may comprise type z derivatized porous silicon. Each type of derivatization may be selected so that when the three storage means are brought into contact with the skin surface, and conditions are such that sweating occurs, the storage means each selectively bind to a different component of the sweat. In this way different sweat elements and compounds can be collected simultaneously.

In an alternative embodiment multiple storage means may be formed on a single silicon substrate. Each storage sample may comprise a different type of derivatized porous silicon that selectively binds to a different sweat component. The silicon substrate may comprise bulk crystalline silicon.

Measurement of the Change in Conductivity of a Storage Sample of Porous Silicon as a Result of the Presence of Sweat FIG. 6 shows a schematic diagram of a body fluid collection device, generally indicated by 61, according to the invention. The body fluid collection device 61 comprises a first storage sample of porous silicon 62, and attachment means 63, two electrodes 63, 64, a biasing means 65, and an ammeter 66. The first storage sample of porous silicon 62 is attached to the surface of the skin 67 of a subject 67 by the attachment means 63. The subject is made or allowed to sweat while the body fluid collection device is in contact with the skin, and the resulting change in the conductivity is monitored by means of the ammeter.

The Effect of Partial Oxidation on the Stability of a Storage Sample of Porous Silicon in Simulated Human Sweat A third storage sample of porous silicon was prepared by the following method, which will be referred to as "method C":

A 0.005 ohm cm wafer was anodised in 20% ethanoic HF at 5 mA cm$^{-2}$ for 120 seconds and then 50 mA cm$^{-2}$ for 10 minutes. Half of the anodised water was then partially oxidised by thermal treatment in air at 500 C. for 30 minutes to yield the third storage sample of porous silicon.

Any sample referred to, in this specification, as a "third storage sample of porous silicon", should be taken as a sample of porous silicon prepared by method C.

A fourth storage sample of porous silicon was prepared by the following method, which will be referred to as "method D":

The half of the anodised wafer that was not oxidised in method B, was stored in air at room temperature for a period of 12 days to yield the fourth sample of porous silicon.

Any sample referred to, in this specification, as a "fourth sample of porous silicon" should be taken as a sample of porous prepared by method D.

Segments of the third and fourth storage samples of porous silicon were then incubated in simulated human sweat at 25 C. The simulated human sweat was prepared in accordance with ISO standard (3160/2) and is described by J P Randin in J. Biomed. Mater. Res. 22, 649 (1988). The simulated human sweat comprises NaCl (20 g/litre), NH4Cl (17.5 g/litre), urea (5 g/litre), acetic acid (2.5 g/litre), and lactic acid (15 g/litre). The pH of the simulated human sweat was adjusted to 6.5 by addition of NaOH.

FIG. 7(*a*) is a cross-sectional SEM image of the third storage sample of porous silicon. FIG. 7(*b*) shows a higher magnification image of the same sample, the image being of the lower porosity region close to the surface of the sample. FIG. 7(*c*) shows the third storage sample of porous silicon after 9 days immersion in simulated sweat. There is substantially no corrosion resulting from this period of immersion.

FIG. 7(*d*) shows the fourth storage sample of porous silicon, after 9 days immersion in simulated sweat. As can be seen from the SEM image, significant corrosion has occurred.

The Effect of Applying an Electrical Bias to the Storage Properties of a Storage Sample of Porous Silicon FIG. 8 shows a SIMS profile for a second storage sample of porous silicon after 40 minutes immersion in simulated human sweat to which a lithium ions have been added to make the concentration of lithium ions in the simulated human sweat equal to 2 millimolar. The lithium ions were added in the form of lithium nitrate. A comparsion of the sodium and lithium profiles of FIG. 8 with those of FIG. 3 shows that the simulated sweat has substantially not entered the high porosity porous layer 81.

FIG. 9 shows a storage means 91 that has been partly immersed in simulated human sweat 92. The storage means comprises a first storage sample of porous silicon 93, and a portion of bulk crystalline silicon 54, the porous silicon 93 being in contact with the bulk crystalline silicon 54. The first storage sample of porous silicon 93 may comprise derivatized porous silicon. An electrode 95 is attached to the portion of bulk crystalline silicon and maintained at a constant potential relative to earth by means of a power supply 96. The simulated human sweat 92 comprises an aqueous solution of NaCl (20 g/litre), NH4Cl (17.5 g/litre), urea (5 g/litre), acetic acid (2.5 g/litre), and lactic acid (15 g/litre). The pH of the solution was adjusted to 5.5 by the addition of NaOH. This corresponds to ISO standard (3160/2), which is described by J P Randin in J Biomed Mater Res 22, 649 (1988). Experiments were performed at potentials between 0V and +−50 V over periods of immersion between 10 minutes and 1 week.

After the period of immersion is complete the first storage sample of porous silicon 93 is removed from the simulated human sweat 92 and subjected one or more of the following analytical techniques: MALDI, SIMS, and SEM. The sample may also be analyzed by one of: photoluminsecence spectroscopy, relectivity spectroscopy, absorance spectroscopy, and fluorescence spectroscopy. MALDI may be used to determine the uptake of organic sweat molecules, SIMS may be used to determine the uptake of sweat elements, SEM may be used to determine the corrosion or absence of corrosion by the simulated human sweat. The spectroscopic analysis may be used to determine the presence of a sweat sample on or in the first storage sample of porous silicon 93.

FIG. 10 also shows a SIMS depth profile for a second storage sample of porous silicon, to which an anodic bias has been applied (2 mA cm$^{-2}$ at 1.5 V for 10 minutes). The profile was obtained after immersion, at the anodic potential, for 10 minutes in simulated human sweat to which a lithium ions, in the form of lithium nitrate. The lithium ions are present in the simulated human sweat at a concentration of 2 millimolar. The FIG. 10 results are markly different from those of FIG. 9. The sodium level throughout the high porosity layer 81 has risen by three orders of magnitude, and the lithium concentration in the high porosity layer has risen by more than three orders of magnitude. By contrast the organic components of the simulated sweat have been impeded by the low porosity layer 82.

FIG. 11 shows the SIMS depth profiles for the second storage sample of porous silicon, after a cathodic electrical bias (2 mA cm$^{-2}$ at 3.0 V) has been applied to the sample for 10 minutes. The cathodic bias was also found to promote wetting, but with more diffusion like properties over these short time scales.

The Effect of Partial Oxidation on the Wettability of a Storage Sample of Porous Silicon A fifth storage sample of porous silicon was prepared by the following method, which will be referred to as "method E":

A second storage sample was partially oxidized in air at 500 C. for 30 minutes to yield the fifth sample of porous silicon.

References in this specification to a "fifth storage sample of porous silicon" should by taken as reference to a storage sample of porous silicon prepared by method E.

The fifth storage sample of porous silicon was incubated in simulated human sweat containing lithium ions (the concentration of lithium ions in the simulated human sweat being equal to 2 m mol/litre) for 40 minutes. FIG. 12 show a SIMS plot for a fifth storage sample of porous silicon after this immersion in simulated sweat. The FIG. 12 results show improved wetting by cations, relative to the second storage sample of porous silicon, without any application of an electrical bias. The FIG. 12 sodium and lithium profiles are very similar, in terms of shape of the profile, to those shown in FIG. 10. The result shows that partial oxidation of a sample of porous silicon may improve wetting of the sample by cations present in simulated human sweat.

Relationship Between SIMS Measurements and Concentration of a Sweat Element

A fifth storage sample of porous silicon was immersed in simulated human, containing lithium ions, sweat for 10 minutes. The concentration of lithium ions in the simulated human sweat solution was 0.2 m mol/litre, which is ten times lower than for the simulated human sweat used to obtain the FIG. 12 results. The SIMS results for the lower lithium concentration are shown in FIG. 13.

A comparsion of the FIG. 12 and FIG. 13 results shows that the concentration of lithium present in the fifth storage sample of porous silicon is approximately ten times lower in the FIG. 13 sample than in the FIG. 12 sample. In other words the FIGS. 12 and 13 results show that there is an approximately linear relationship between concentration of lithium in the simulated sweat solution and the concentration in the storage sample of porous silicon.

FIG. 13 also shows that lithium signal corresponding to the 0.2 m mol/litre concentration is approximately 200 times the background signal. This result, combined with the approximate linearity between the lithium concentration in simulated sweat, and the SIMS signal from the storage sample of porous silicon, suggests that lithium concentrations as low as 1 micro mol/litre might be detectable. Indeed, if lithium concentrations were to accumulate over time, concentrations much lower that this could be detected, by collecting the lithium over a period greater that the ten minute duration of the FIG. 13 experiment.

The Effect of Human Sweat on a Storage Sample of Porous Silicon

Once the first storage sample of porous silicon 24 has been in contact with the skin of a human subject for a period of between 10 minutes and 1 week, under conditions which cause the area of skin in contact with the storage sample to sweat, it is removed from the skin and subjected to one of the following analytical techniques: MALDI, SIMS, and SEM. The sample may also be analyzed by one of: photo-luminescence spectroscopy, reflectivity spectroscopy, absorance spectroscopy, and flurorescence spectroscopy. MALDI may be used to determine the uptake of organic sweat molecules, SIMS may be used to determine the uptake of sweat elements, SEM may be used to determine the correrosion or absence of corrosion by the sweat. The spectoscopy analysis may be used to determine the presence of a sweat sample on or in the storage sample of porous silicon 24.

A fifth storage sample of porous silicon, having a length and width each of 10 mm was attached to the front of a wrist of a human subject. The storage sample was attached to the wrist by an elastoplast for 40 minutes, with its porous face in direct contact with the skin of the wrist. During this period the subject performed gentle exercise. FIG. 14 shows the SIMS depth profiles for the prominent sweat components: Na, K, Ca, Mg, and C, together with the trace elements: Fe, Cu, Pb, and Li. A comparsion of FIG. 14 with that of FIG. 12, shows that the level of carbon in the fifth storage sample of porous silicon, as a result of attachment to a human subject, has risen by 100 times relative to exposure to simulated human sweat.

Measurement or Detection of a Sweat Sample After Separation from a Storage Sample of Porous Silicon After the sweat sample has been collected on a storage sample of porous silicon, it may be separated from the sample of porous silicon for example by immersing the silicon in a solvent.

The sweat sample my then be measured or detected by one of the following techniques: high pressure liquid chromatograpy (HPLC), enzymen immuno assay (EIA), atomic absorption spectroscopy (AAS), anodic stripping voltammetry (ASV), and gel electrophoresis (GE).

EIA may be used for peptides and is described in U.S. Pat. No. 6,132,975, AAS may be used for trace metals and is described in Clinica Chimica Acta Vol 2312, P23–28 (1994), ASV may be used for trace metals and is described in Sci Total Environ. Vol 60, p263–271 (1987), GE may be used for proteins and is described in Analyt. Biochem. Vol 131, p520–524 (1983).

An alternative method by which the sweat sample may be combined with a liquid is by dissolving a porous silicon storage sample of porous silicon, on or in which a sweat sample has been collected, by reacting the porous silicon with a suitable alkali. For example porous silicon may be dissolved by aqueous NaOH, and by aqueous KOH. The alkali aqueous solution of the porous silicon and sweat sample, may then analyzed by an appropriate technique.

What is claimed is:

1. An attachable body fluid collection device comprising at least one storage means for, when in use, storing a body fluid sample secreted by a body fluid secreting surface, the at least one storage means comprising porous silicon, porous silicon oxide, or a combination of porous silicon and porous silicon oxide, wherein the collection device further comprises means for applying a bias to at least part of the silicon such that, when in use, the bias causes a rate of body fluid sample deposition on the storage means to be higher than that at ground potential.

2. A fluid collection device according to claim 1, wherein the device further comprises attachment means for attaching the at least one storage means to part of a surface of an animal or human body.

3. A fluid collection device according to claim 1, wherein the device further comprises a backing layer, the backing layer having a structure and composition such that, when in use, it isolates the at least one storage means from environment surrounding the collection device.

4. A fluid collection device according to claim 1, wherein the silicon comprises porous silicon oxide.

5. A fluid collection device according to claim 4, wherein the silicon comprises partially oxidized porous silicon having a structure and composition such that it is substantially un-corroded after contact with human sweat for a period between 10 minutes and 10 days.

6. A fluid collection device according to claim 4, wherein the silicon comprises partially oxidized porous silicon having a structure and composition such that it is substantially un-corroded after contact with simulated human sweat for an interval of between 5 minutes and one month.

7. A method of collecting a body fluid sample from an animal or human comprising:
   (i) placing a sample of porous silicon or porous silicon oxide, or a combination thereof, in fluid communication with part of a body fluid secreting surface of the animal or human;
   (ii) allowing or causing the animal or human to express the body fluid sample; and
   (iii) collecting the body fluid sample on or in at least part of the sample,
   wherein the collecting further comprises applying a bias to the sample in such a manner that a rate of collection of the body fluid sample is accelerated, relative to the rate of collection, when the sample is at ground potential.

8. A method according to claim 7, wherein the method further comprises analyzing the body fluid sample that has been collected on or in at least part of the sample.

9. A method according to claim 8, wherein the analyzing further comprises detecting a body fluid sample that has been collected on or in at least part of the sample, by one or more of the following techniques: MALDI, SIMS, measurement of photoluminescence efficiency, measurement of photoluminescence spectra, reflective spectroscopy, absorance spectroscopy, and measurement of photoluminescence decay time.

10. A method according to claim 8, wherein the analyzing further comprises analyzing the body fluid sample that has been collected on at least part of the sample for a period between 1 hour and 24 hours.

11. A method according to claim 8, further comprising separating the body fluid sample from the sample prior to the analyzing, by bringing the at least part of the sample into contact with a solvent, so that at least part of the body fluid sample passes into the solvent.

12. A method according to claim 11, wherein the separating further comprises applying a bias to the sample in such a manner that the bias increases the rate at which the sweat sample moves from the sample into the solvent, relative to the rate when the sample is at ground potential.

13. A method according to claim 7, wherein (i) the placing comprises placing a sample in fluid communication with skin of an animal or human, (ii) the allowing or causing comprises allowing or causing the animal or human to sweat; and (iii) the collecting comprises collecting a sample of sweat on or in at least part of the sample.

14. A method according to claim 7, wherein (i) the placing further comprises bringing the sample into contact with the fluid secreting surface.

15. A method according to claim 7, wherein the silicon comprises partially oxidized porous silicon, and (i) the placing comprises placing the sample of partially oxidized porous silicon in fluid communication with part of the body fluid secreting surface.

* * * * *